United States Patent [19]

Iwane et al.

[11] Patent Number: 5,019,656

[45] Date of Patent: May 28, 1991

[54] PROCESS FOR PREPARING P-HYDROXYBENZYL ALCOHOL

[75] Inventors: Hiroshi Iwane; Takahiro Sugawara; Naoki Suzuki, all of Ami, Japan

[73] Assignee: Mitsubishi Petrochemical Co., Ltd., Tokyo, Japan

[21] Appl. No.: 485,482

[22] Filed: Feb. 27, 1990

[30] Foreign Application Priority Data

| Mar. 4, 1989 [JP] | Japan | 1-52608 |
| Jul. 11, 1989 [JP] | Japan | 1-178241 |
| Dec. 6, 1989 [JP] | Japan | 1-315159 |

[51] Int. Cl.$^5$ .................. C07C 37/20; C07C 39/10
[52] U.S. Cl. .................. 568/764; 568/715; 568/716; 568/727; 568/811
[58] Field of Search ............... 568/715, 764, 727, 716, 568/811, 846

[56] References Cited

U.S. PATENT DOCUMENTS

| 4,192,959 | 3/1980 | Bauer et al. | 568/764 |
| 4,238,629 | 12/1980 | Bauer et al. | 568/764 |

FOREIGN PATENT DOCUMENTS

| 63001 | 7/1960 | Australia | 568/764 |
| 017851 | 10/1990 | European Pat. Off. | 568/764 |
| 0071044 | 6/1978 | Japan | 568/764 |
| 286341 | 12/1986 | Japan | 568/764 |

Primary Examiner—Werren B. Lone
Attorney, Agent, or Firm—Oblon, Spivak, McClelland, Maier & Neustadt

[57] ABSTRACT

A process for preparing p-hydroxybenzyl alcohol or a derivative thereof comprising reacting a phenol and a formaldehyde source under a basic condition is disclosed, wherein the reaction is carried out in an alcoholic organic solvent in the presence of a crown ether. The process achieves high selectivity toward the para position without involving high cost.

13 Claims, No Drawings

PROCESS FOR PREPARING P-HYDROXYBENZYL ALCOHOL

FIELD OF THE INVENTION

This invention relates to a process for preparing p-hydroxybenzyl alcohol and a derivative thereof. More particularly, it relates to a process for preparing p-hydroxybenzyl alcohol or a derivative thereof by reacting a phenol and a formaldehyde source under a basic condition.

p-Hydroxybenzyl alcohol and its derivatives are important as a starting material for synthesizing various useful organic compounds, such as pharmaceuticals, agricultural chemicals, and antioxidants. For example, p-hydroxybenzyl alcohol is very useful as a starting material for producing p-hydroxybenzylaldehyde, 4,4'-dihydroxydiphenylmethane, etc.

BACKGROUND OF THE INVENTION

Industrial production of hydroxybenzyl alcohols has conventionally been carried out by reaction between phenol with formaldehyde in the presence of a basic catalyst without a solvent. Rarely has the reaction been effected in a nonaqueous solvent.

Known processes for obtaining p-hydroxybenzyl alcohol on an industrial scale include a process comprising reacting phenol and formaldehyde to obtain a mixture of p-hydroxybenzyl alcohol and o-hydroxybenzyl alcohol and separating the mixture into each isomer by, for example, extraction as disclosed in JP-A-54-36223 (the term "JP-A" as used herein means an "unexamined published Japanese patent application").

In the reaction between phenol and formaldehyde in the presence of a basic catalyst, a production ratio of p-hydroxybenzyl alcohol to o-hydroxybenzyl alcohol (hereinafter referred to as para/ortho production ratio) is generally no higher than 1.0.

Techniques so far proposed for increasing the production ratio of p-hydroxybenzyl alcohol in the reaction between phenol and paraformaldehyde include (1) addition of a polyalkylene ether to the system containing a strongly basic catalyst as disclosed in JP-A-56-16423 and (2) use of an organic nitrogen compound having at least two nitrogen atoms per molecule as a basic catalyst as disclosed in JP-A-56-16424. Nevertheless, the proportion of the para-compound in the resulting mixed hydroxybenzyl alcohol as obtained by these processes is still lower than that of the ortho-compound, i.e., 49% and 47%, respectively.

It has recently been proposed to selectively synthesizing p-hydroxybenzyl alcohol using cyclodextrin and modified cyclodextrin as reported in *J. C. S.*, p. 652, c.c. (1988). According to this process, β-cyclodextrin, sodium hydroxide, and formaldehyde are used in amounts of from 20 to 40 times, 50 times, and 40 times, respectively, the amount of the starting phenol. Therefore, although the para/ortho production ratio reaches 15.7, the process is of no industrial advantage from the economical standpoint.

SUMMARY OF THE INVENTION

An object of this invention is to provide a process for selectively preparing industrially useful p-hydroxybenzyl alcohol or a derivative thereof at low cost.

The present invention provides a process for preparing p-hydroxybenzyl alcohol or a derivative thereof comprising reacting a phenol and a formaldehyde source under a basic condition, wherein the reaction is carried out in an alcoholic organic solvent in the presence of a crown ether.

DETAILED DESCRIPTION OF THE INVENTION

A crown ether, a general term for macrocyclic polyethers, includes metallic ions or other cations with a considerable force in water or an organic solvent. There are many cases in organic synthesis in which the metallic ion inclusion ability of crown ethers is taken advantage of to generate a naked anion having high reactivity in a non-polar solvent thereby causing a specific reaction. The feature of the present invention resides in that selectivity of the reaction between a phenol and a formaldehyde source toward production of p-hydroxybenzyl alcohol or a derivative thereof is greatly increased by using a crown ether in the presence of an alcoholic solvent.

Phenols which can be used in this invention include phenol, a 2-substituted phenol, a 3-substituted phenol, a 2,3-disubstituted phenol, a 2,5-disubstituted phenol, a 3,5-disubstituted phenol, and a 2,3,5-trisubstituted phenol. Substituents of substituted phenols are not particularly limited and include, for example, a saturated or unsaturated hydrocarbon group, an aryl group, an alkoxyl group, a carboxyl group, a sulfo group, an amino group, and a halogen atom.

Specific examples of substituted phenols are o-cresol, m-cresol, 2-ethylphenol, 3-ethylphenol, 2,5-dimethylphenol, 2-hydroxyphenol, 3-phenylphenol, guaiacol (2-methoxyphenol), salicylic acid, 2-hydroxyphenethyl alcohol, 3-hydroxyphenethyl alcohol, 2-chlorophenol, and 2-bromophenol.

Preferred of them are phenol and 2-substituted phenols. Preferred examples of substituents for the 2-substituted phenols include an alkyl group having 1 to 5 carbon atoms and an alkoxy group having 1 to 5 carbon atoms in view of the reaction rate.

Formaldehyde sources which can be used in the present invention include formalin, paraformaldehyde, a hemiformal of a lower alcohol, and a hemiformal of a polyhydric alcohol having from 2 to 5 carbon atoms, with paraformaldehyde and a hemiformal of a lower alcohol being preferred. While formalin is employable as long as used in a small amount, selectivity to the para position is slightly reduced according as a water content in the reaction system increases.

It is particularly preferable to use a hemiformal of an alcohol obtained by sublimating (or gasifying) paraformaldehyde in order to remove glycol aldehyde from paraformaldehyde and absorbing the vapor into an alcohol. By using the hemiformal as a refined formaldehyde source as described, the reaction rapidly proceeds to attain a high yield while suppressing side reactions such as formose formation and Cannizzaro reaction.

It is convenient to use a formaldehyde sublimate obtained by heating 80% paraformaldehyde at a temperature of about 80° to 90° C. under reduced pressure of from 15 to 20 mmHg by means of a Mill's sublimating tube.

It is preferable that the thus purified paraformaldehyde is scraped off, and dissolved in an alcohol in a concentration of from 1 to 2 mol/l, said alcohol having dissolved therein a trace amount of sodium hydroxide in a concentration of about 0.1 mol%, and Molecular Sieve is added to the solution for preservation. The trace amount of sodium hydroxide is for accelerating dissolution of paraformaldehyde in the alcohol. The alcohol may be heated to a temperature at which the alcohol is not refluxed, in place of dissolving sodium hydroxide in the alcohol.

Alternatively, it is convenient to use a formaldehyde sublimate obtained by heating 80% paraformaldehyde at a temperature of about 200° C. in an inert gas (e.g., nitrogen) stream at atmospheric pressure and blowing the vapor into an alcohol heated to a temperature at which the alcohol is not refluxed.

In preserving the solution, Molecular Sieve, etc. is preferably added thereto.

Industrial preparation of the formaldehyde sublimate is generally effected by heating 80% paraformaldehyde to a high temperature in an inert gas (e.g., nitrogen) stream and blowing the vapor into a heated solvent (e.g., alcohol). In this case, sufficient cares should be taken to keep the passage for the vapor to a blowing tube sufficiently warm. Otherwise, the vapor tends to crystallize and obstruct the passage. The solvent in which the vapor is dissolved is preferably the same as that used for the reaction of the present invention.

The formaldehyde source is preferably used in an amount of from 0.1 to 10 equivalents, and more preferably from 0.5 to 3 equivalents, to the phenol as reduced to formaldehyde.

Basic catalysts for creating a basic condition for the reaction include metal-containing bases having higher basicity than the phenol, such as metal hydroxides, e.g., sodium hydroxide and potassium hydroxide, metal alkoxides, e.g., sodium methoxide, sodium ethoxide, and potassium t-butoxide, and metal hydrides, e.g., sodium hydride.

The basic catalyst is preferably used in an amount of from 0.01 to 10 equivalents, more preferably from 0.1 to 1.2 equivalents, and the most preferably from 0.9 to 1.0 equivalents, to the phenol.

Crown ethers which can be used in the present invention are macrocyclic polyethers having ability of including metallic cations in the ring thereof and include crown ethers of various ring sizes, preferably those having 4 to 6 oxygen atoms in the ring thereof, such as a so-called 18-crown ether-6 (e.g., 18-crown ether-6, dibenzo-18-crown ether-6, dicyclohexano-18-crown ether-6, benzo-18-crown ether-6, and cyclohexano-18-crown ether-6), a 15-crown ether-5 corresponding to these 18-crown ethers-6, and a 24-crown ether-8; various crown ethers having a binaphthol or aromatic group in the ring thereof; and various functionalized crown ethers such as 1,4,7,10,13-pentaoxacyclohexadecan-15-ol and 15-methyl-1,4,7,10,13-pentaoxacyclohexadecan-15-ol, with the 18-crown ether-6, the 15-crown ether-5 and the 24-crown ether-8 being preferred. Fixed crown ethers such as high polymers containing the above-described crown ethers are also included in the crown ethers according to the present invention.

Various methods for fixing crown ethers are known (for example, refer to Michio Hiraoka, *Crown Kagobutsu*, Kodansha). General fixed crown ethers include addition polymerization type high polymeric crown ethers synthesized from dibenzo-18-crown-6 and aldehyde, polycondensation type crown ether polymers synthesized from diaminobenzo-18-crown-6 and a diacid chloride, diisocyanate, etc., and polyvinyl crown ether compounds.

The crown ether is preferably used in an amount of from 0.1 to 10 equivalents, more preferably from 0.8 to 5 equivalents, to the basic catalyst.

In the process of this invention, para position selectivity of the reaction is markedly increased by using an alcohol as a solvent. It is considered that the reaction to the ortho position is sterically inhibited by formation of an ion pair of a phenolate anion and metallic cation included by the crown ether and solvation of a phenolate anion with alcohols. Protonic solvents solvating an anion generally include water and alcohols, but presence of water in the reaction system according to the present invention unfavorably reduces the effect of the alcohol of increasing para position selectivity. Accordingly, the water content in the reaction solvent should be 10% by weight or less, preferably 6% by weight or less, and more preferably 3% by weight or less. If it exceeds 10%, the positional selectivity is greatly reduced.

The alcoholic organic solvent which can be used in the present invention include alkyl alcohols having from 1 to 10 carbon atoms, preferably from 1 to 4 carbon atoms, e.g., methanol, ethanol, n-propanol, isopropanol, n-butanol, i-butanol, and t-butanol; polyhydric alcohols, e.g., ethylene glycol and 2,3-butanediol; benzyl alcohol and like alcohols containing an aromatic group; and mixtures thereof. Preferred of them are lower alcohols, e.g., ethanol, n-propanol, isopropanol and isobutanol in view of higher selectivity and higher reaction rate.

To increase solubility of crown ethers, the above-described alcohol solvent can be used in combination with a non-alcoholic organic solvent. Suitable non-alcoholic organic solvents include aromatic solvents, e.g., benzene, toluene, and xylene; aliphatic solvents, e.g., pentane, hexane, and heptane; halogenated alkanes, e.g., chloroform, dichloromethane, and dichloroethane; amides, e.g., dimethylacetamide and dimethylformamide; sulfoxides, e.g., dimethyl sulfoxide; and nitriles, e.g., acetonitrile and benzonitrile.

The mixing ratio of the non-alcoholic organic solvent is not more than 70% by weight, and preferably not more than 30% by weight, based on the total solvent. If it exceeds 70% by weight, the reaction rate would be decreased. The alcoholic organic solvent preferably has an alcohol content of at least 30% by weight. In general, it is more preferable to use a solvent solely comprising an alcohol or a mixture of alcohols.

The reaction is preferably carried out in a nitrogen atmosphere. The reaction is generally carried out using from 0.1 to 10 mols, preferably from 0.5 to 3 mols, of a phenol per liter of a solvent comprising the above-described alcoholic organic solvent solely or in combination and from 0.01 to 100 equivalents, preferably 0.1 to 10 equivalents, more preferably from 0.5 to 3 equivalents, of a formaldehyde source as reduced to formaldehyde based on the phenol. The basic catalyst is preferably used in an amount of from 0.01 to 10 equivalents, more preferably from 0.1 to 1.2 equivalent based on the phenol, and the crown ether is preferably used in an amount of from 0.1 to 100 equivalents, more preferably from 0.8 to 5 equivalents, based on the basic catalyst.

The reaction temperature preferably ranges from 0 to 130° C., more preferably from 30° to 80° C. The reaction time depends on the reaction temperature and the kind of the solvent used. For example, it is preferably from 6 to 100 hours at a reaction temperature of 60° C. As the temperature decreases, para selectivity is slightly increases whereas the reaction rate is reduced accordingly.

The reaction pressure is not particularly limited, but normal pressure is usually employed. The reaction may also be conducted under pressure of not higher than 100 bar or under reduced pressure.

In carrying out the reaction, a phenol, a basic catalyst base, and a crown ether are first added to a solvent usually in a nitrogen atmosphere, and the mixture is stirred under heating to dissolve all the content. In case of using a resinous crown ether, the resin is dispersed in the solvent. After the temperature is returned to room temperature (not higher than 30° C.), a formaldehyde source is then added thereto, the atmosphere is again displaced with nitrogen, and the reaction is conducted at a prescribed temperature.

If desired, the resulting reaction product is purified and separated into a para-compound and an ortho-compound by extraction, crystallization, or the like technique.

While p-hydroxybenzyl alcohol is used as a starting material for synthesizing various organic compounds, where the resulting p-hydroxybenzyl alcohol is further subjected to reaction with a phenol, the above-obtained reaction product may be used for the reaction as it is without separation. For instance, for the production of 4,4'-dihydroxydiphenylmethane, the reaction according to the present invention may be performed by using a phenol in excess, that is, using from 0.01 to 5 equivalents, preferably from 0.1 to 1 equivalent, of a formaldehyde source based on the phenol. After completion of the reaction, the reaction mixture is made acidic to thereby obtain 4,4'-dihydroxydiphenylmethane at a high selectivity.

The present invention is now illustrated in greater detail by way of Examples, but it should be understood that the present invention is not construed as being limited thereto. In Examples, all the percents are by weight unless otherwise specified. Yields, selectivities, and para/ortho ratios were calculated from the following equations:

$$\text{Yield} = \frac{\text{Number of Moles of Formaldehyde Consumed}}{\text{Number of Moles of Formaldehyde Charged}} \times 100\ (\%)$$

$$\text{Selectivity} = \frac{\text{Number of Moles of Each Product}}{\text{Total Number of Moles of Phenols Produced}} \times 100\ (\%)$$

$$\text{Selectivity*} = \frac{\text{Number of Moles of Each Product}}{\text{Total Number of Moles of Dihydroxy-diphenylmethanes Produced}} \times 100\ (\%)$$

$$\frac{\text{Para/Ortho}}{\text{Production Ratio}} = \frac{\text{Selectivity of Para-Compound}}{100 - (\text{Selectivity of Para-Compound})}$$

(*APPLICATION EXAMPLE)

EXAMPLE 1

In a 15 ml-volume glass-made pressure reactor were charged 5 ml of isopropanol, 0.517 g (5.49 mmol) of phenol, 0.211 g (5.01 mmol) of 95% sodium hydroxide, and 1.462 g (5.53 mmol) of 18-crown ether-6. After displacing the atmosphere with nitrogen, the mixture was heated at 80° C. with stirring. On confirming that the content was dissolved, the temperature was returned to room temperature (not higher than 30° C). To the mixture was added 0.094 g (2.5 mmol) of 80% paraformaldehyde, and the atmosphere was again displaced with nitrogen. The mixture was heated at 60° C. for 12 hours while stirring to complete the reaction.

The yield based on formaldehyde was 22.5%. The product comprised p-hydroxybenzyl alcohol, o-hydroxybenzyl alcohol, and dimethylolphenol, and the selectivity of p-hydroxybenzyl alcohol was 80.8%. From the fact that selectivity of p-hydroxybenzyl alcohol in the initial stage of the reaction where dimethylolphenol was not produced was 83.3%, the para/ortho production ratio in the reaction was found to be 4.99.

EXAMPLE 2

The procedure of Example 1 was repeated, except that the reaction was conducted at 40° C. for 12 hours.

The yield based on formaldehyde was 9.9%. The product comprised p-hydroxybenzyl alcohol and o-hydroxybenzyl alcohol, and the selectivity of p-hydroxybenzyl alcohol was 87.8%. Accordingly, the para/ortho production ratio was 7.20.

When the reaction was continued for 72 hours in total, the yield reached 37.1%.

COMPARATIVE EXAMPLE 1

The procedure of Example 1 was repeated, except for using no 18-crown ether-6 and continuing the reaction for 24 hours.

The yield based on formaldehyde was 15.8%. The product comprised p-hydroxybenzyl alcohol, o-hydroxybenzyl alcohol, and dimethylolphenol, and the selectivity of p-hydroxybenzyl alcohol was 22.6%. From the fact that the selectivity of p-hydroxybenzyl alcohol in the initial stage of the reaction where dimethylolphenol was not produced was 24.2%, the para/ortho production ratio was found to be 0.32.

EXAMPLES 3 TO 8

The procedure of Example 1 was repeated, except for replacing isopropanol used in Example 1 with the solvent shown shown in Table 1 below. The reaction results are also shown in Table 1.

TABLE 1

| Example No. | Solvent | Yield* (%) | Para/Ortho Production Ratio |
|---|---|---|---|
| 3 | ethanol | 9.7 | 3.20 |
| 4 | n-propanol | 13.3 | 4.11 |
| 5 | n-butanol | 18.5 | 2.37 |
| 6 | i-butanol | 14.7 | 3.63 |
| 7 | t-butanol | 38.5 | 2.52 |
| 8 | i-propanol/methanol = 5/1 (by volume) | 9.2 | 3.80 |

Note: *Based on formaldehyde.

COMPARATIVE EXAMPLES 2 TO 4

The procedure of Example 1 was repeated, except for replacing isopropanol with each of the non-alcoholic solvents shown in Table 2 below. The reaction results obtained are also shown in Table 2.

TABLE 2

| Comparative Example No. | Solvent | Yield* (%) | Para/Ortho Production Ratio |
|---|---|---|---|
| 2 | toluene | 9.3 | 1.04 |
| 3 | dioxane | 28.9 | 0.19 |

TABLE 2-continued

| Comparative Example No. | Solvent | Yield* (%) | Para/Ortho Production Ratio |
|---|---|---|---|
| 4 | 95% dioxane aqueous solution | 16.0 | 0.46 |

Note: *Based on formaldehyde.

EXAMPLE 9

The procedure of Example 2 was repeated, except for using 15-crown ether-5 as a crown ether.

The yield based on formaldehyde was 10.6%. The product comprised p-hydroxybenzyl alcohol, o-hydroxybenzyl alcohol, and dimethylolphenol, and the selectivity of p-hydroxybenzyl alcohol was 82.4%. From the fact that the selectivity of p-hydroxybenzyl alcohol in the initial stage of the reaction where dimethylolphenol was not produced was 84.7%, the para-/ortho production ratio was found to be 5.54.

EXAMPLE 10

In a 15 ml-volume glass-made pressure reactor were charged 5 ml of isopropanol, 0.514 g (5.47 mmol) of phenol, 0.209 g (4.97 mmol) of sodium hydroxide, and 1.449 g (5.47 mmol) of 18-crown ether-6. After displacing the atmosphere with nitrogen, the mixture was heated at 80° C. while stirring. On confirming that the content was completely dissolved, the temperature was returned to room temperature (not higher than 30° C). To the mixture was added 1.62 ml of a pure hemiformal solution prepared by dissolving sublimated paraformaldehyde in isopropanol at a concentration of 1.54 mol/l (formaldehyde content: 2.49 mmol), and the atmosphere was again displaced with nitrogen, followed by heating at 50° C. for 40 hours while stirring to complete the reaction.

The yield based on formaldehyde was 98.6%. The product comprised p-hydroxybenzyl alcohol, o-hydroxybenzyl alcohol, and dimethylolphenol, and the selectivity of p-hydroxybenzyl alcohol was 72.3%. From the fact that the selectivity of p-hydroxybenzyl alcohol in the initial stage of the reaction where dimethylolphenol was not produced was 86.8%, the para-/ortho production ratio was found to be 6.58.

EXAMPLE 11

The procedure of Example 10 was repeated, except that the reaction was conducted at 40° C. for 96 hours.

The yield based on formaldehyde was 85.1%. The product comprised p-hydroxybenzyl alcohol, o-hydroxybenzyl alcohol, and dimethylolphenol, and the selectivity of p-hydroxybenzyl alcohol was 75.7%. From the fact that the selectivity of p-hydroxybenzyl alcohol in the initial stage of the reaction where dimethylolphenol was not produced was 88.2%, the para-/ortho production ratio was found to be 7.47.

EXAMPLE 12

In a 15 ml-volume glass-made pressure reactor were charged 5 ml of isopropanol, 0.555 g (5.13 mmol) of o-cresol, 0.216 g (5.13 mmol) of sodium hydroxide, and 1.787 g (5.13 mmol) of 18-crown ether-6. After displacing the atmosphere with nitrogen, the mixture was heated at 80° C. with stirring. On confirming that the content was completely dissolved, the temperature was returned to room temperature (not higher than 30° C.). To the mixture was added 3.82 ml of a pure hemiformal solution prepared by dissolving sublimated paraformaldehyde in isopropanol at a concentration of 0.67 mol/l (formaldehyde content: 2.56 mmol), and the atmosphere was again displaced with nitrogen, followed by heating at 50° C. for 43 hours while stirring.

The yield based on formaldehyde was 91.8%. The product comprised 4-hydroxymethyl-2-methylphenol, 6- hydroxymethyl-2-methylphenol, and 4,6-dihydroxymethyl-2-methylphenol at a selectivity of 80.3%, 7.4%, and 12.3%, respectively.

From the fact that the selectivity of 4-hydroxymethyl- 2-methylphenol in the initial stage of the reaction where a dimethylol compound was not produced was 92.1%, the para/ortho production ratio was found to be 11.66.

COMPARATIVE EXAMPLE 5

The procedure of Example 12 was repeated, except for using no crown ether.

The yield based on formaldehyde was 86.0%. The product comprised 4-hydroxymethyl-2-methylphenol, 6-hydroxy- methyl-2-methylphenol, and 4,6-dihydroxymethyl-2-methylphenol at a selectivity of 25.6%, 53.8%, and 20.6%, respectively.

From the fact that the selectivity of 4-hydroxymethyl-2-methylphenol in the initial stage of the reaction where a dimethylol compound was not produced was 36.2%, the para/ortho production ratio was found to be 0.57.

EXAMPLE 13

In a 15 ml-volume glass-made pressure reactor were charged 5 ml of isopropanol, 0.521 g (4.81 mmol) of m-cresol, 0.205 g (4.81 mmol) of sodium hydroxide, and 1.708 g (4.81 mmol) of 18-crown ether-6. After displacing the atmosphere with nitrogen, the mixture was heated at 80° C. with stirring. On confirming that the content was completely dissolved, the temperature was returned to room temperature (not higher than 30° C.). To the solution was added 3.58 ml of a pure hemiformal solution prepared by dissolving sublimated paraformaldehyde in isopropanol at a concentration of 0.67 mol/l (formaldehyde content: 2.40 mmol), and the atmosphere was again displaced with nitrogen, followed by heating at 50° C. for 19 hours while stirring to complete the reaction.

The yield based on formaldehyde was 89.9%. The product comprised 4-hydroxymethyl-3-methylphenol, 6-hydroxy- methyl-3-methylphenol, 2-hydroxymethyl-3-methylphenol, and dihydroxymethyl compounds (e.g., 4,6-dihydroxymethyl-3-methylphenol) at a selectivity of 61.1%, 20.4%, 4.1%, and 14.4%, respectively.

From the fact that the selectivity of 4-hydroxymethyl-3-methylphenol in the initial stage of the reaction where dimethylol compounds were not produced was 75.1%, the para/ortho production ratio was found to be 3.03.

COMPARATIVE EXAMPLE 6

The procedure of Example 13 was repeated, except for using no 18-crown ether-6.

The yield based on formaldehyde was 84.3%. The product comprised 4-hydroxymethyl-3-methylphenol, 6-hydroxy- methyl-3-methylphenol, 2-hydroxymethyl-3-methylphenol, and dihydroxymethyl compounds (e.g., 4,6-dihydroxymethyl-3-methylphenol) at a selectivity of 7.3%, 57.2%, 11.0%, and 24.5%, respectively.

From the fact that the selectivity of 4-hydroxymethyl-3-methylphenol in the initial stage of the reaction where no dimethylol compounds were produced was 12.3%, the para/ortho production ratio was found to be 0.14.

EXAMPLE 14

In a 15 ml-volume glass-made pressure reactor were charged 5 ml of isopropanol, 0.614 g (4.92 mmol) of guaiacol (2-methoxyphenol), 0.209 g (4.92 mmol) of sodium hydroxide, and 1.746 g (4.92 mmol) of 18-crown ether-6. After displacing the atmosphere with nitrogen, the mixture was heated to 80° C. with stirring. On confirming that the content was completely dissolved, the temperature was returned to room temperature (not higher than 30° C.). To the mixture was added 3.67 ml of a pure hemiformal solution prepared by dissolving sublimated paraformaldehyde in isopropanol at a concentration of 0.67 mol/l (formaldehyde content: 2.46 mmol). The atmosphere was again displaced with nitrogen, and the mixture was heated at 50° C. for 14 hours while stirring to complete the reaction.

The yield based on formaldehyde was 97.6%. The product comprised 4-hydroxymethyl-2-methoxyphenol, 6-hydroxymethyl-2-methoxyphenol, and 4,6-dihydroxymethyl-2-methoxyphenol at a selectivity of 77.7%, 9.4%, and 12.8%, respectively.

From the fact that the selectivity of 4-hydroxymethyl-2-methoxyphenol in the initial stage of the reaction where a dimethylol compound was not produced was 91.1%, the para/ortho production ratio was found to be 10.24.

COMPARATIVE EXAMPLE 7

The procedure of Example 14 was repeated, except for using no 18-crown ether-6.

The yield based on formaldehyde was 99.1%. The product comprised 4-hydroxymethyl-2-methoxyphenol, 6-hydroxy-methyl-2-methoxyphenol, and 4,6-dihydroxymethyl-2-methoxyphenol at a selectivity of 11.5%, 73.6%, and 14.9%, respectively.

From the fact that the selectivity of 4-hydroxymethyl-2-methoxyphenol in the initial stage of the reaction where a dimethylol compound was not produced was 14.2%, the para/ortho production ratio was found to be 0.17.

APPLICATION EXAMPLE

In a 15 ml-volume glass-made pressure reactor were charged 5 ml of isopropanol, 0.544 g (5.78 mmol) of phenol, 0.242 g (5.78 mmol) of sodium hydroxide, and 1.533 g (5.78 mmol) of 18-crown ether-6, and the atmosphere was displaced with nitrogen. The mixture was heated to 80° C. with stirring. On confirming that the content was completely dissolved, the temperature was returned to room temperature (not higher than 30° C.). To the mixture was added 0.86 ml of a pure hemiformal solution prepared by dissolving sublimated paraformaldehyde in isopropanol at a concentration of 0.67 mol/l (formaldehyde content: 0.578 mmol). The atmosphere was again displaced with nitrogen, and the mixture was heated at 50° C. for 24 hours while stirring to complete the reaction.

The product in the reaction mixture was found to comprise p-hydroxybenzyl alcohol and o-hydroxybenzyl alcohol by liquid chromatography. The selectivity of p-hydroxybenzyl alcohol was 88.3%, the conversion of formaldehyde was 100% (the absence of formaldehyde was confirmed by gas chromatography), and the yield based on formaldehyde was 85.6%.

To the reaction mixture was added a 12N hydrochloric acid aqueous solution so as to contain 0.05 mmol excess of an acid. The atmosphere was displaced with nitrogen, and the resulting acidic solution was heated at 80° C. for 4 hours while stirring.

After cooling to room temperature (not higher than 30° C.), the reaction mixture was analyzed and, as a result, found to contain no hydroxybenzyl alcohol and comprise 4,4'-dihydroxydiphenylmethane, 2,4'-dihydroxydiphenylmethane, and 2,2'-dihydroxydiphenylmethane at a selectivity of 80.2%, 19.8%, and 0.1%, respectively, with slight polynuclear compounds.

While the invention has been described in detail and with reference to specific embodiments thereof, it will be apparent to one skilled in the art that various changes and modifications can be made therein without departing from the spirit and scope thereof.

What is claimed is:

1. A process for preparing p-hydroxybenzyl alcohol or a derivative thereof comprising reacting a phenol selected from phenol, a 2-substituted phenol, a 3-substituted phenol, a 2,3-disubstituted phenol, a 2,5-disubstituted phenol, a 3,5-disubtituted phenol, and a 2,3,5-trisubstituted phenol and a formaldehyde source selected from formalin, paraformaldehyde, a hemiformal of a lower alcohol, and a hemiformal of a polyhydric alcohol having from 2 to 5 carbon atoms in the presence of basic catalyst, wherein the reaction is carried out in an alcoholic organic solvent in the presence of a crown ether having ability of including metallic cations in the ring thereof.

2. A process as claimed in claim 1, wherein said phenol is phenol.

3. A process as claimed in claim 1, wherein said formaldehyde source is paraformaldehyde or a hemiformal of a lower alcohol.

4. A process as claimed in claim 1, wherein said formaldehyde source is formaldehyde prepared by sublimating paraformaldehyde.

5. A process as claimed in claim 1, wherein a phenol to formaldehyde equivalent ratio is from 100:1 to 1:100.

6. A process as claimed in claim 1, wherein a basic catalyst is used in an amount of from 0.01 to 10 equivalents to the phenol.

7. A process as claimed in claim 1, wherein said crown ether is selected from crown ethers having 4 to 6 oxygen atoms in the ring thereof.

8. A process as claimed in claim 1, wherein said crown ether is used in an amount of from 0.1 to 100 equivalents to a basic catalyst for creating the basic condition.

9. A process as claimed in claim 1, wherein said alcoholic organic solvent has an alcohol content of at least 30% by weight and a water content of not more than 10% by weight.

10. A process as claimed in claim 1, wherein said alcoholic organic solvent contains an alkyl alcohol having not more than 4 carbon atoms.

11. A process as claimed in claim 1, wherein said reaction is at a temperature of from 30° to 80° C.

12. The process of claim 1, wherein said phenol is phenol or 2-substituted phenols, wherein said substitution is selected from the group consisting of an alkyl group having 1 to 5 carbon atoms and an alkoxy group having 1 to 5 carbon atoms.

13. The process of claim 1, wherein said crown ether is selected from the group consisting of 18-crown ether-6, dibenzo-18-crown ether-6, dicyclohexano-18-crown ether-6, benzo-18-crown ether-6, cyclohexano-18-crown ether-6, 15-crown ether-5, dibenzo-15-crown ether-5, dicyclohexano-15-crown ether-5, benzo-15-crown ether-5, cyclohexano-15-crown ether-5, 24-crown ether-8, dibenzo-24-crown ether-8, dicyclohexano-24-crown ether-8, benzo-24-crown ether-8, cyclohexano-24-crown ether-8, 1,4,7,10,13-pentaoxacyclohexadecan-15-ol, and 15-methyl-1,4,7,10,13,pentaoxacyclohexadecan-15-ol.

* * * * *